United States Patent [19]

Naldoni et al.

[11] Patent Number: 5,324,479
[45] Date of Patent: Jun. 28, 1994

[54] ANALYZER FOR THE DETERMINATION OF THE PHENOTYPE AND THE ABO BLOOD GROUP

[75] Inventors: Guido Naldoni; Umberto Basagni, both of Florence, Italy

[73] Assignee: Menarini Industrie Farmaceutiche Riunite SRL, Florence, Italy

[21] Appl. No.: 383,032

[22] Filed: Jul. 21, 1989

[30] Foreign Application Priority Data

Jul. 29, 1988 [IT] Italy ................... 48252 A/88

[51] Int. Cl.$^5$ ................... G01N 33/00; G01N 21/01
[52] U.S. Cl. ................... 422/63; 73/864.22; 422/64; 422/65; 422/67; 422/82.09
[58] Field of Search ................... 422/63, 64, 65, 82.09, 422/73; 436/43, 47, 49; 73/864.22, 864.23, 864.24; 366/273

[56] References Cited

U.S. PATENT DOCUMENTS

| 3,942,952 | 3/1976 | Atwood | 73/864.22 |
|---|---|---|---|
| 4,101,284 | 7/1978 | Difiglio et al. | 422/100 |
| 4,318,885 | 3/1982 | Suzuki et al. | 73/864.22 |
| 4,322,216 | 3/1982 | Lillig et al. | 422/64 |
| 4,503,011 | 3/1985 | Hubeau | 422/73 |
| 4,727,033 | 2/1988 | Hijikata et al. | 422/65 |
| 4,728,500 | 3/1988 | Higo | 422/73 X |
| 4,861,554 | 8/1989 | Sakuma | 422/65 |
| 4,876,069 | 10/1989 | Jochimsen | 316/273 |

FOREIGN PATENT DOCUMENTS 0212663 3/1987 European Pat. Off. ........... 422/100

Primary Examiner—James C. Housel
Assistant Examiner—Arlen Soderquist
Attorney, Agent, or Firm—Beveridge, DeGrandi, Weilacher & Young

[57] ABSTRACT

An analyzer for the determination of the ABO unit and the phenotype, said analyzer comprising a rotatable plate carrying sample-bearing test-tubes and dilution test-tubes arranged along concentric circumferences; a dispensing needle which is movable by mechanical means between a washing position, a position for drawing a sample, a position for diluting the sample and a position for introducing the sample into a reading well; a station for washing said needle; a conveyor unit for conveying carrier members which are provided with 12 reaction wells to a position for receiving diluted or the undiluted samples from the dispensing needle; an automatic feeder that feeds small balls into each of the wells during the forward motion along the conveyor unit; mechanical means for transferring the carrier member to a reading zone; a unit that meters the specific antiserum or red cells into each one of the wells; and an optical reading device that horizontally reads the transmittance of each one of the wells, starting from the moment when antiserum or red cells are introduced; and a processor for functionally controlling the analyzer and for issuing an estimate of the results of the analyses.

21 Claims, 15 Drawing Sheets

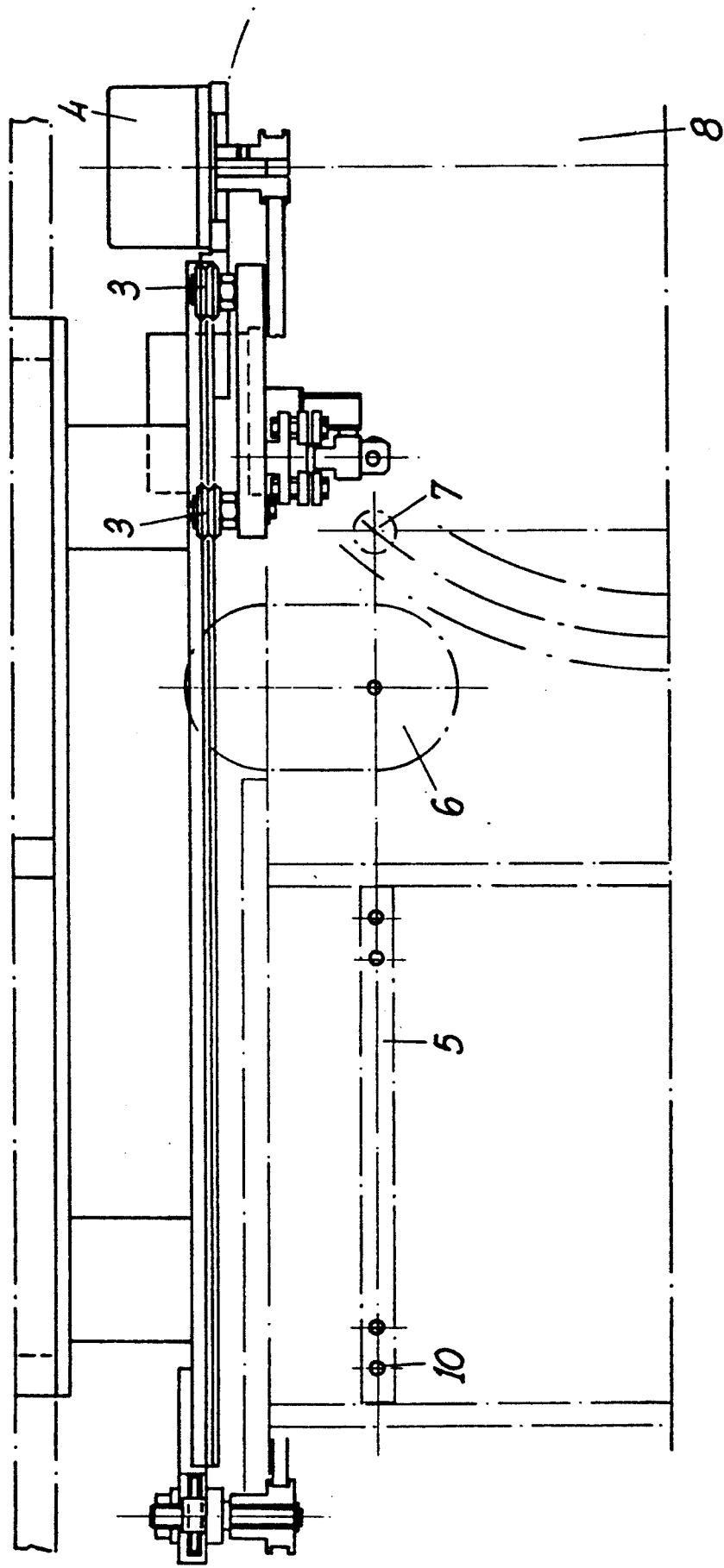

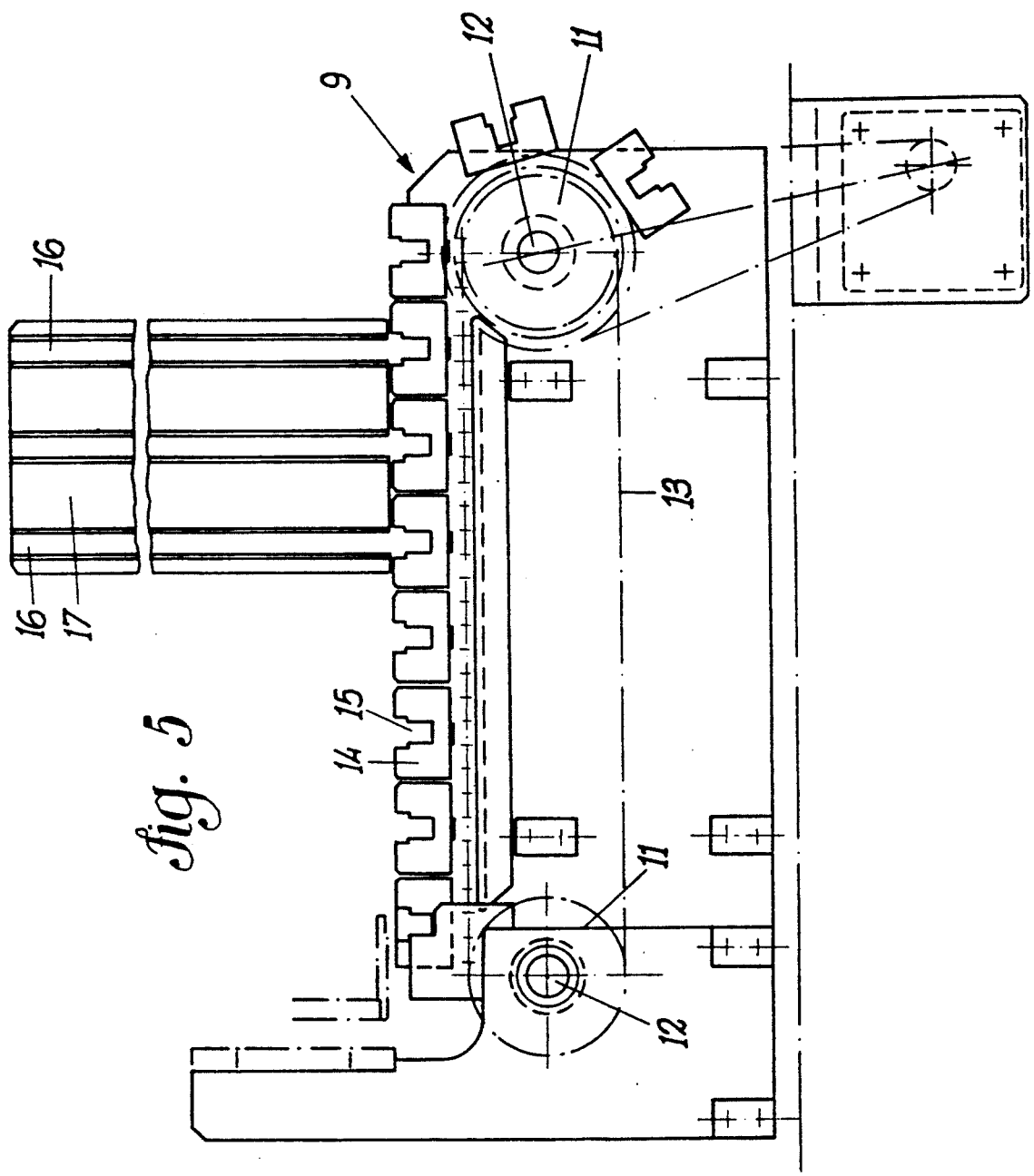

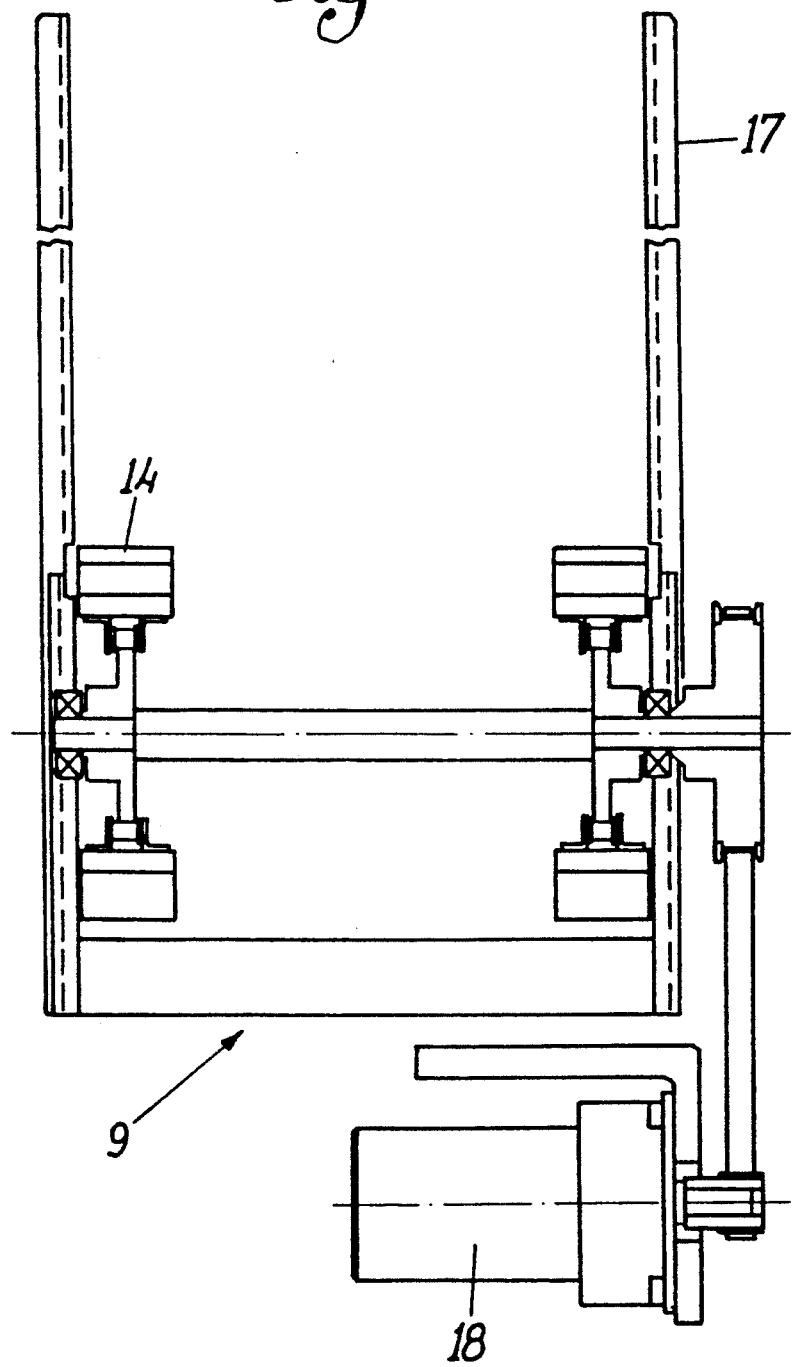

ANALYZER FOR THE DETERMINATION OF THE PHENOTYPE AND THE ABO BLOOD GROUP

BACKGROUND OF THE INVENTION

This invention relates to an analyzer for the determination of the ABO unit and of the phenotype of blood.

More particularly, this invention relates to an analyzer of the type mentioned above, which is fully automatic and less expensive than the automatic analyzers available at the present time, though it is capable of performances similar to those of the latter.

As is well known, blood units are permanent characteristics of each individual and are determined by the genes that originate antigen and antibody systems.

An antigen represents a substance that, if introduced into an individual, stimulates an immune reaction characterized by the production of specific proteins: the antibodies. Thus, an antibody is a substance that reacts specifically with that antigen which has stimulated its production.

For the blood units, antigens are molecules which are immunologically reactive and are present on the surface of the red cells of each individual.

The blood unit antibodies are plasmatic proteins that can be classified as "natural antibodies", so that it is not possible to put into evidence a specific antigenic stimulus that has generated its product, and as "immune antibodies", which are synthesized by an organism in response to the introduction of a determined erythrocyte antigen.

The introduction of erythrocyte antigens with the subsequent production of immune antibodies and the consequent immune reaction can occur, in particular, during transfusion and pregnancy.

Accordingly, it is evident and well known to those who are skilled in the art that the determination of the antigen-antibody systems of blood unit is very important as regards the theory and practice of blood transfusion.

The most important blood units system, whose knowledge is fundamental for the efficiency and safety of blood transfusion, is the ABO system.

A further blood system of remarkable interest from an immunohematological standpoint is the Rhesus system (or Rh system), which collects together a wide series of different antigens.

Moreover, other minor antigen systems are present on the surface of the erythrocytes, said systems having less immune power than the blood unit systems mentioned above.

The contact between erythrocyte antigens and their corresponding antibodies can give rise to a reaction that is called agglutination and represents the most efficient and simplest way to make the antigen-antibody reaction visible.

Such agglutination reaction is exploited for the determination of blood units in normal laboratory practice.

In agglutination, two steps can be distinguished: in the first step the antibody molecule combines with the erythrocyte membrane antigens (the sensitization step), while in the second step the antibody forms bridge-links among different erythrocytes so determining the proper agglutination step.

At the present time, three methods are mainly employed for the determination of blood units. They are the manual method, the semi-automatic method (or the micromethod), and the automatic method.

The main manual procedures for determining blood units are:

the slide agglutination test: this is the test commonly adopted for the determination of the ABO and the Rh blood unit systems. It consists of a rapid test that is carried out with suspended red cells at 40-50% in plasma or an autologous serum, and is performed at room temperature if complete IgE type sera (reagents) are employed or if modified IgG type antibody-containing sera are employed, and at a temperature of about 37° C. in the case of incomplete antibody sera which are made capable of giving agglutination by the hyperproteic medium;

the test-tube agglutination test: this is a test mainly employed for the determination of erythrocyte antigens with common incomplete sera. It is carried out with 5-10% suspended erythrocytes in a physiological solution, and the reading is performed after centrifuging the reagents.

Micromethods or semi-automatic methods make use of relatively concentrated erythrocytes suspensions containing very low amounts of the test-serum.

The procedure employed in micromethods is almost fully automatic.

In particular, a remarkable waste of time occurs with semiautomatic analyzers as the technician is to follow the various steps of the whole process, performing for instance the dispensing or pipetting operation and the transfer to the measuring operations.

The automatic method for determining the blood unit is carried out with very expensive analyzers, which as a consequence are inaccessible to the average or small laboratories.

Some analyzers of such type will be disclosed below, with particular reference to their technical features and performance.

GROUPAMATIC 2000 (KONTRON)

This is a 18-channel, automatic analyzer for the determination of blood units and of other immunohematological parameters, and is based on the photometric reading of agglutination.

The analyzing rate is 2,000 reactions/hour, with the possibility of analyzing 120 samples/hour over 18 channels, or 240 samples/hour over 9 channels.

It can be employed for:

A) The ABO determination, with discrimination of the weak variants of the antigen A (A3, Am, etc.);

B) The determination of Rh and of Du;

C) Screening of irregular antibodies by means of different techniques:
the saline medium
the monomolecular medium
bromelin-methylcellulose (BMC)
trypsin-polybrene-citrate (TPC)
low ionic strength hyperproteic medium (LIHP)

D) The determination of the anti A and anti B immune antibodies;

E) Screening of syphilis;

F) The determination of the Rh, Kell, Lewis, etc. phenotypes; and

G) The analysis of special antibodies (for instance, antitetanic antibodies).

Preparation of samples: Samples, collected together with EDTA into test-tubes, are centrifuged separately and put manually on the Groupamatic, in a driving system consisting of 120 containers assembled in series of 12:1 white and 11 black.

A sample tube and a dilution tube are associated with each container. A chain will take the samples through the following stations:

1) the dilution station;
2) the sampling and loading station; and
3) the station for identifying the medium.

The dilution system: the dilution probe is inserted automatically into the sample tube. A pump sucks a volume of packed red cells, then it expels that volume together with a bromelin saline medium when the needle is positioned in front of the proper dilution tube.

The volumes of the red cells and of the physiological solution are adjustable by means of a computer program.

The washing operation between two samples is carried out externally by means of a washing ring and internally by the physiological solution employed for the dilution.

The sampling system: The samples go step by step towards the sampling station. There, the diluted red cells and the plasma are sucked through a double needle in the pipe and are taken to the proper cuvettes.

The reactants (antisera, special solutions, red cell-test) are stored in sets of a 9 beakers which are put on special racks.

The pipes carry the reagents which are removed from the beakers by the pump, into the proper cuvettes.

The recording of the identification number: The identification number of the samples is read by an optical system and transferred to the computer for storing the same.

The loading of samples: The immunohematological and serum reactions occur within the 216 cuvettes of the reaction disc.

There are 9 cuvettes and 24 sectors for each disc. The operator can make the decision of employing:

two sectors for each sample and 12 samples for each disc (up to 18 reactions for each sample); or one sector for each sample and 24 samples for each disc (up to 9 reactions for each sample).

On the average, 10 reaction discs per hour are read.

The disc is loaded automatically by means of a "reagent" pump and a "sample" pump, said pumps distributing from 10 to 140μliters per cuvette and from 1 to 5 reagents (optional).

An injection rotatable plate loads the first disc onto the first multitest station that causes in turn the loading of the second disc. Such a movable plate also allows the reagents to be loaded during the cycle.

The first stage consists in loading two sample sectors (diluted red cells and plasma) each time.

Two movable injectors deliver the selected volumes into each cuvette. The rapid loading of reagents occurs when the loading of the samples has been completed.

The processing occurring at the reaction disc: the multitest station generates at the disc:

a slow rotation (indexation);
a step-by-step motion for taking each cuvette sector below the injection plate and the photometers;
a fast rotation (centrifuging); and
a horizontal agitation.

The recording of reactions: at the end of each reaction cycle, the 9-cell photometer is positioned above the disc, where the reactions inside the cuvettes are read, one sector each time.

The photometric reading is based on the amount of light transmitted through the peripheral part and through the central part of the cuvette.

The results of such measurements are transmitted to the control unit and combined with the respective identification number.

The reactions are interpreted according to a pre-established logic that is shown on the display and is printed with its identification number.

The visual reading of the reactions: each sector on the disc corresponds to a specific reaction.

It is possible to observe the reactions both on the multitest station that can be lighted and on the disc itself after the same has been removed from the instrument.

The operator substitutes the disc with a clean disc and he starts a new cycle. The disc already employed can be rinsed or washed.

The photometric system: The control unit puts in correlation the contrast between the central and the peripheral light transmission measurements. The contrast is zero when the reaction is negative, and it increases when the reaction strength increases.

A set of thresholds is assigned to each channel, said thresholds discriminating the positive, the weakly positive and negative as well as the normal and abnormal reactions.

The abnormal reactions can be read visually by the operator and the result can be recorded on the file of the results by means of the video-terminal printer.

Such procedure keeps the number of samples to be tested again to a minimum.

The preparation of reactants: sera commercially available, once diluted in physiological solution or in macromolecular media, can be stored at 4° C. for a week. The working schedule for determining the working dilution on a Groupamatic is as follows:

1) e.g.: anti-A titred 1/64 can be employed on said instrument when diluted to 4% concentration in saline medium or 2% in a macromolecular medium; and 2) anti-D titred 1/256 with bromelin-treated red cells is employed at 3% dilution in physiological solution.

TECHNICON AUTOGROUPER 16C

This is a 16-channel analyzer, which channels are programmed at the operator's choice for direct ABO and for indirect type determination; Rh type determination; phenotype determination; detection of irregular antibodies; detection of dangerous O donors; syphilis test. There is one channel for control functions.

It is possible to analyze 120 samples/hour and this analyzer allows complete computerization both of interpretation and of printing.

The identification of the sample occurs through the CODABAR system and laser scanning, and the possibility is provided of interfacing with a central computer.

The analyzer also allows flexible reagents and techniques to be employed on the basis of the selection of the reagents and of the agglutination temperature, i.e. 37° C. or 18° C.

This instrument is provided with dedicated automatic alarm systems and it shows a better monitor operation. Means are provided for signalling strong agglutinations.

The quantitative estimation of the single channel is also possible: if required, this is obtained through the measurement of the peak (height) of the channel selected.

The test-tubes containing the samples plus ACA or bar-marked EDTA are centrifuged and housed inside the chain "bandolier".

A probe double system sucks the upper portion (the plasma) and the lower portion (red cells).

Red cells are diluted automatically with physiological solution and are treated with enzymes in order to increase their sensitivity.

The main channel of the red cells is divided into sub-channels for determining ABO types and for direct determination of Rh.

The proper antisera are formed inside the channel together with PVP or methylcellulose in order to increase the formation of the agglutinate (rouleaux).

The suspension of samples is kept by air segmentation. The agglutinated materials formed within the reaction loops are dispersed by the successive addition of physiological solution and by a short resolution time.

The various agglutinates that are deposited into a button are sucked off (decanted) in two different moments.

The flow is then freed from air bubbles and the optical density of the remainder liquid is determined continuously by means of an optical device.

The plasma channel is in turn divided for the indirect type determination against red cells and for the determination of antibodies, the detection of dangerous O's and the ART test of syphilis.

Moreover, the "Filter Paper Backup" is provided, which is an optional system for the visual identification and backup of the ODU (Optical Detection Units) system in the case of electronic faults.

At the first decanting operation, the agglutinated materials are deposited onto filter paper instead of conveying them to the waste discharge point.

The selection of temperatures: the channels are kept at constant temperatures of 37° C. or 18° C. according to the operator's frequency.

The red cell suspension and the antisera are mixed and kept at a constant temperature of 12° C.

The very brain of the unit consists of an INTEL microprocessor that is so programmed as to also receive signals from the 16 optical reading systems to decide about the ABO and Rh grouping and about the occurrence or not of an agglutination in each channel.

After making such decisions, the microprocessor correlates the results so obtained with the sample number which is read by a laser source on a bar code and transmitted from an interface to the same microprocessor.

The information is passed to the printer that gives a list of each sample according to the identification bar code and to its sequential number.

Similar signals for each channel are passed from the microprocessor to the recorder for their quantification.

The agglutination strength depends on the peak height. The positive signals are also transmitted to the event marker that acts as a monitor and points out the channel phase and as a second signal check.

Moreover, the microprocessor selects the sample washing time of the sampler, selects the discrimination levels of the optical units, functions as a monitor of the instrument performance with the carryover and phase check, and it can be interfaced with any other computer and can be programmed within quite wide limits according to the single uses.

OLYMPUS PK 7100

This automatic analyzer carried out the analyses of 120 samples per hour, and the first sample goes out after one incubation hour at 37° C. It comprises microplates bearing 10 samples and 16 channels. Antisera after suitable dilution and the red cells in suspension are drawn and dispensed automatically by means of 16 syringes.

The twelve cuvettes containing the antisera and the red cells are stirred automatically by a comb-like system.

The sampling system is made up of two needles, the first one of which sucks the plasma while the other one sucks the red cells. The latter are then diluted automatically inside a well, whereas the plasma is diluted inside three different wells.

The analyzer is provided with various programs for defining the analysis profile to be exploited in the determination of the red cell type.

Once the automatic distribution of antisera and/or red cells as well as of the samples to be analyzed has occurred, the microplate is automatically taken into a chamber kept at a constant temperature of 37° C. where the microplate will be kept for an hour.

The microplate is then transferred automatically into the reading seat.

The reading is carried out by means of a photocell (for each channel) that reads the difference in brightness between the central and the peripheral zone of the well (like GROUPMATIC 2000-KONTRON).

Moreover, there is an illuminated plane that allows the visual check of the results given by the machine. The plates can be employed again after accurate washing. There is no graphic detection for checking the existence of the agglutination reaction.

The final report gives just the identification number of the sample and the result obtained. Thus the analyzer in question is a very cumbersome apparatus that is sold at a very high price and that cannot carry out the Coembs test.

As a matter of practice, the automatic analyzers disclosed so far, that are capable of decidedly high technical performances, can be only employed in very large sanitary structures, in particular because of their high production costs that derive mainly from the complex realization of the analyzer which is to allow all analysis required to be performed.

Indeed, this is quite a severe problem, also because of the delicate character of such type of analysis and because of the consequences, which are also of penal kind, of an erroneous result.

Accordingly, it is quite evident that it is important to have an analyzer which, by quality and reliability, is capable of giving performances similar to those of the automatic analyzers commercially available at present, but which can be realized at a cost 3–5 times lower, so that such analyzers will be accessible even to small analytical laboratories.

The Applicant, in order to reach such a technical result, has investigated and realized a fully automatic analyzer, whose "philosophy" of reading of the results, which is completely new in the specific field, though it has been adopted in other fields, has allowed an analyzer to be technically achieved that, though lacking some technical performances of the best automatic analyzers, is structurally simpler and can be manufactured at remarkably reduced costs.

The reading of the results in the semi-automatic and automatic analyzers presently available is realized by determining the number of red cells that have become agglutinated and deposited onto the bottom of the test tubes. This type of reading requires a double determination on the bottom of the test-tube, with a vertical determination (the light coming from the bottom and the reading device being at the top) and a horizontal determination to obtain a complete result.

SUMMARY OF THE INVENTION

The object of the Applicant is that of providing an analyzer that, by exploiting the turbidimetric principles, requires a single reading system and makes the analyzer itself technologically simpler and more competitive economically.

It is a further object of the present invention to supply a completely automatic analyzer that is capable of giving extremely reliable performances as it is structurally and functionally able to signal any dubious result to the operator who can thus repeat the analysis.

Accordingly, it is a specific object of the present invention to provide an analyzer for the determination of the ABO unit and of the phenotype, said analyzer comprising a unit that supplies sample-containing test-tubes and dilution test-tubes; a dispensing needle which is movable through mechanical means between washing positions, positions for drawing the sample, for dilution and for introduction into reaction and reading wells in carrier members; a station for washing said needle; a conveyor unit that carries members provided with at least 4 reaction wells in the position for receiving the diluted or undiluted sample from a dispensing needle; an automatic device for supplying small balls into each reaction well during the forward motion along said conveyor unit; mechanical means that transfer the member bearing the reaction wells to a reading zone; a metering unit that meters the specific antiserum or the red cells into each one of said reaction wells; and optical reading device for determining the optical transmittance in each one the reaction wells beginning from the moment the antiserum or of the red cells are metered into the wells; and a processor for the functional control of the analyzer and providing an estimate of the results of the analysis.

Preferably, each of said carrier members are provided with 12 reaction wells.

In particular, the carrier members provided with reaction wells are of elongated shape or "carrier members" that bear the wells arranged side by side at equal distances.

The conveyor unit can in particular be made up of a conveyor belt or of a chain which can rotate around two axes, some seats being provided on said conveyor for housing said "carrier member" parallel to one another.

One or more vertical suppliers of said carrier members into said seats on the conveyor belt can be provided on said conveyor unit.

The small balls are fed inside each well of each carrier member during the forward motion of the carrier member on the conveyor unit, before the carrier member arrives at the dispensing needle. The balls are fed by means of a gravity feeder which includes a mechanical device that, by causing it to oscillate continuously, allows said small balls to be fed optimally, two of these balls being fed into each well.

The metering unit of the analyzer according to the present invention can preferably include a bottle-bearing plate on which 10 bottles bearing antisera are arranged upside down together with two bottles containing the red cells, the antiserum being drawn from said 10 bottles by means of a two-needle system, one of which sucks the antiserum while the other one introduces air into the bottle, above the level of the antiserum, and the two bottles containing the red cells are provided with mechanical stirring means that prevent the deposit from being formed; moreover, said metering unit is provided with 12 needles for metering the antisera or the red cells into the 12 wells of the carrier member, and mechanical means for sucking said antisera and the red cells.

In particular, the mechanical means consist of a 12-channel peristaltic pump, preferably with three motors having 4 channels each.

At the points where the needles meter antisera and the red cells into the wells of the carrier member, a device can be provided for humidifying said needles, said device being provided with humidifying cuvettes and with a forward-backward motion as well as with a lifting motion, so as to keep said needles wet between successive metering operations.

The reading zone can also be provided with mechanical means for centering the position of said carrier member, said means consisting in particular of two movable pistons that couple to suitable seats in each carrier member.

Also in said reading zone and below each well on the carrier member, some magnets can be provided for keeping said small balls in motion.

The unit that feeds the sample-bearing test-tubes and the dilution test-tubes can consist of a rotatable plate bearing two arrays of concentric test-tubes.

At the point corresponding to the test-tube feeder unit, a bar code reading device can be provided to read codes on each sample-bearing test-tube, thus allowing the sample to be associated with the corresponding patient by the processor.

As the dispensing needle first has to draw from the sample-bearing test-tubes the plasma and then the red cells, it is to be provided with a sensor that detects the moment when the needle is dipped into the plasma independently of the sample level inside the test-tube, only a minimum level being necessarily kept.

BRIEF DESCRIPTION OF THE DRAWINGS

This invention will be disclosed in the following according to some preferred embodiments of the same with particular reference to the figures of the enclosed drawings wherein:

FIG. 2 is a top view of the unit which includes FIG. 1;

FIG. 5 is a side view of the conveyor unit of FIG. 4;

FIG. 6 is a front view of the conveyor unit of FIG. 4;

DETAILED DESCRIPTION

Figure 1:
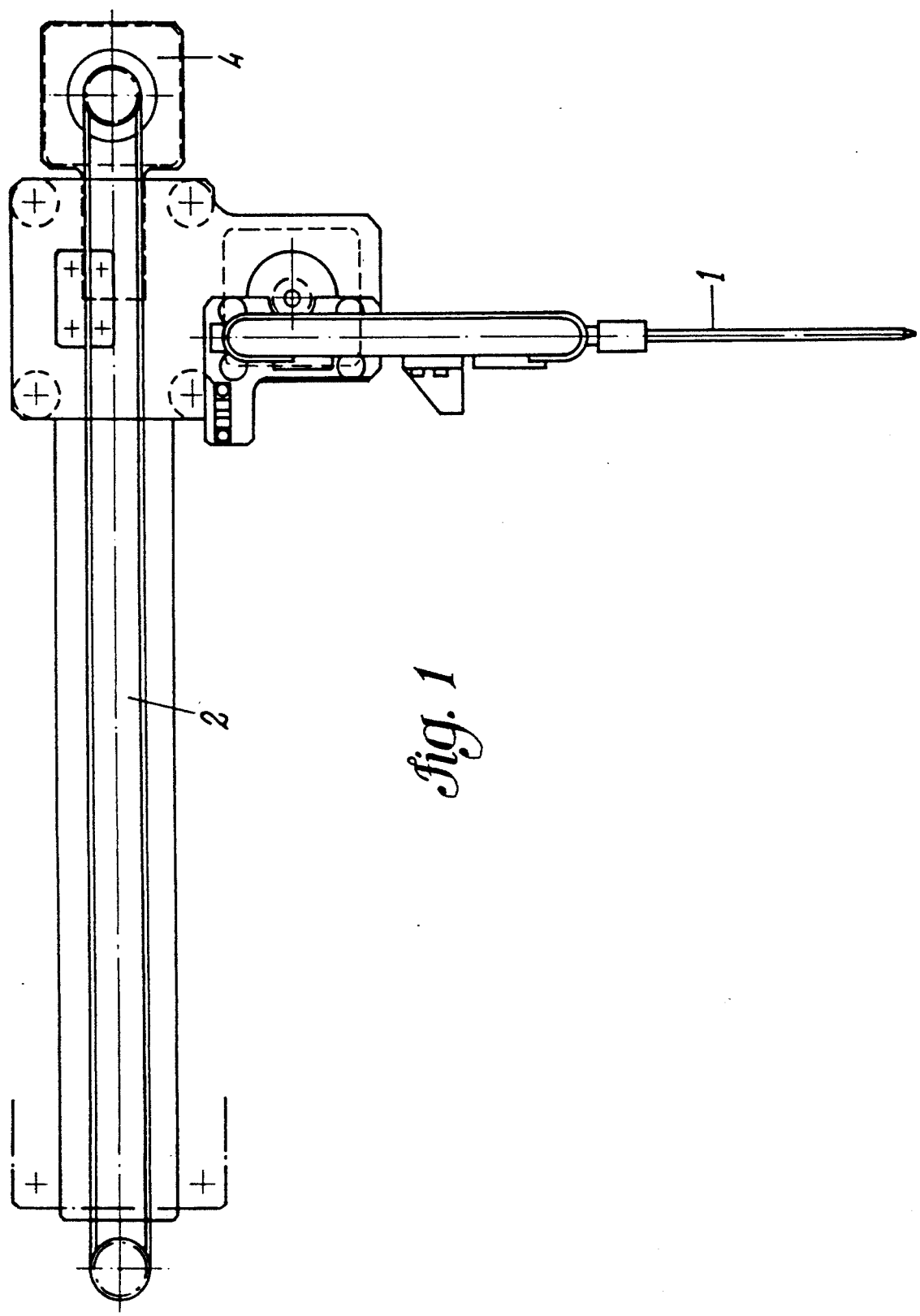
FIG. 1 is a front view of the unit of the drawing and dispensing needles of the analyzer of the present invention.
Figure 3:
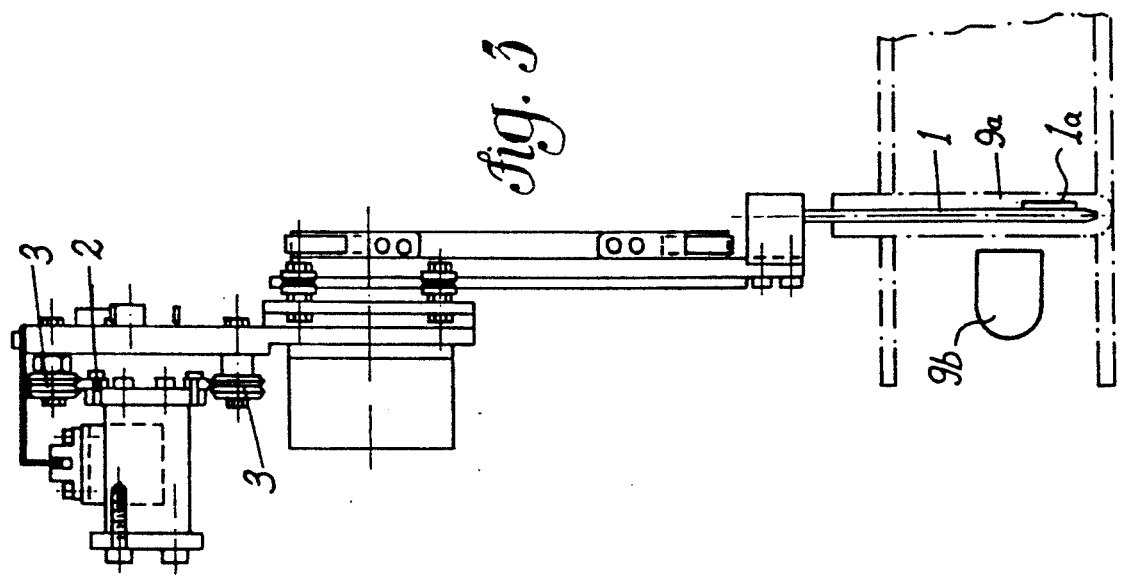
FIG. 3 is a side view of the unit of FIG. 1.
Figure 7A:
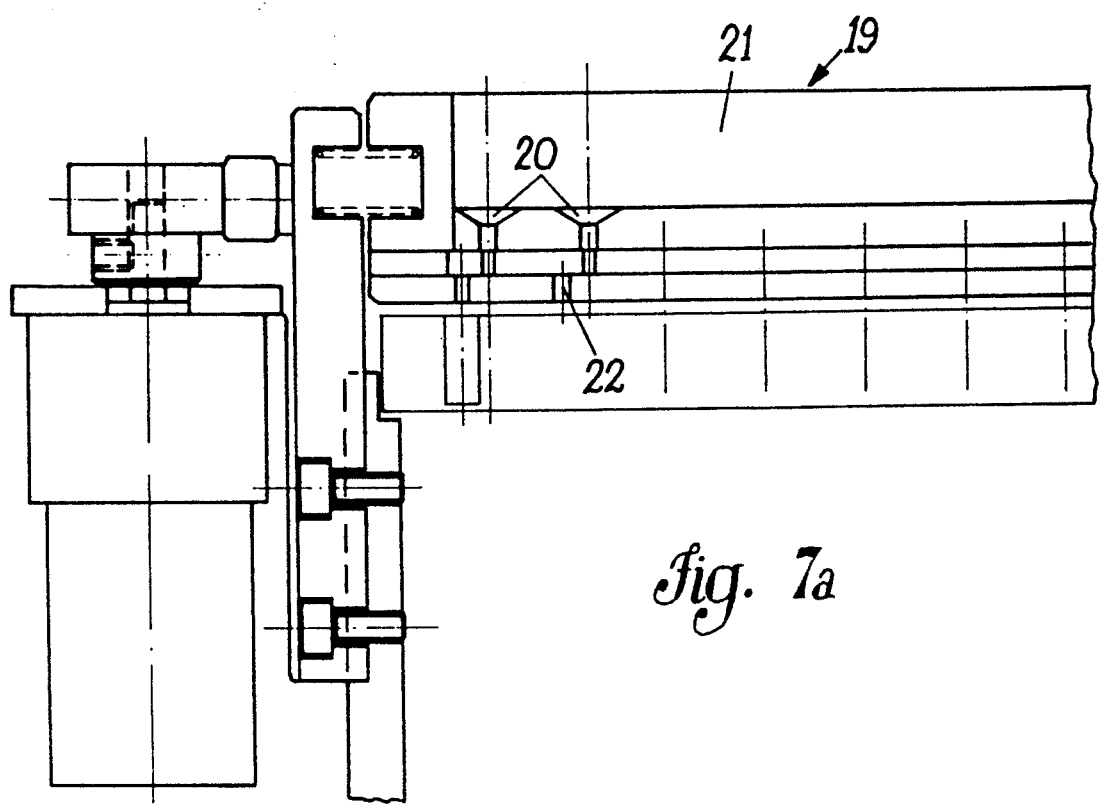
FIGS. 7a and 7b show a front view of the small ball feeder of the analyzer according to the present invention.
Figure 8A:
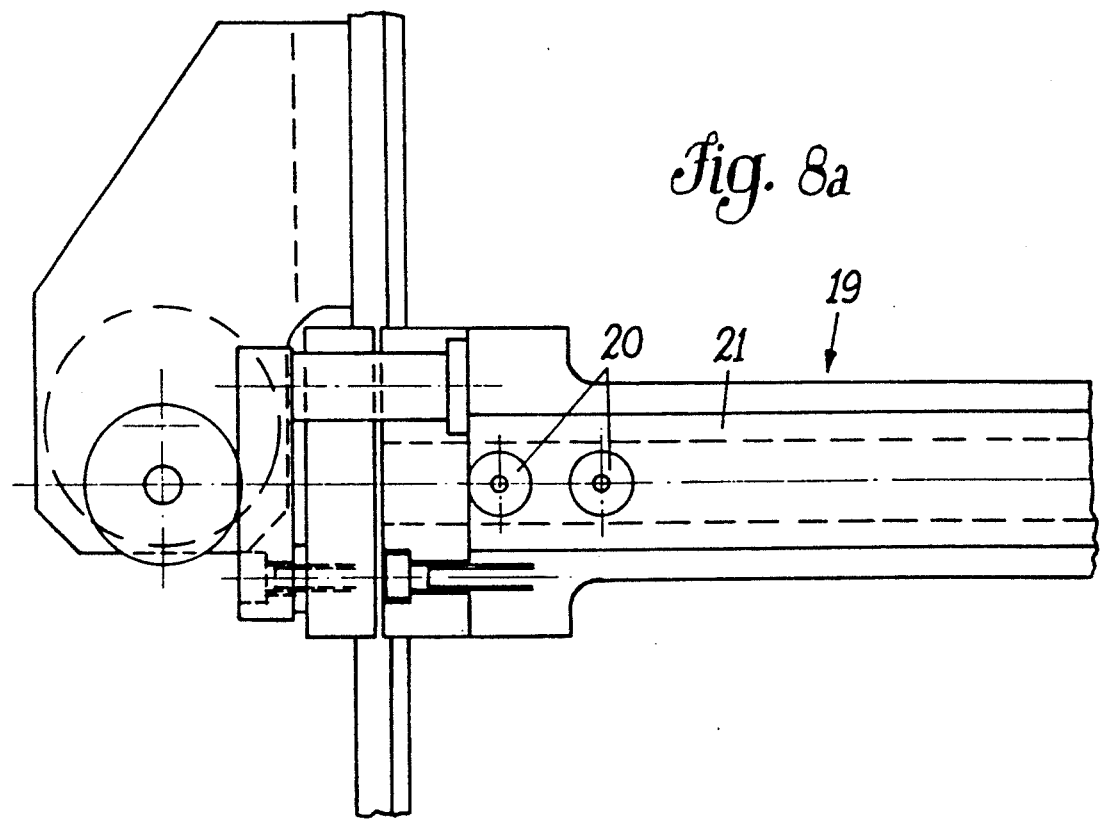
FIGS. 8a and 8b show a plan view of the feeder of FIGS. 7a and 7b.
Figure 7B:
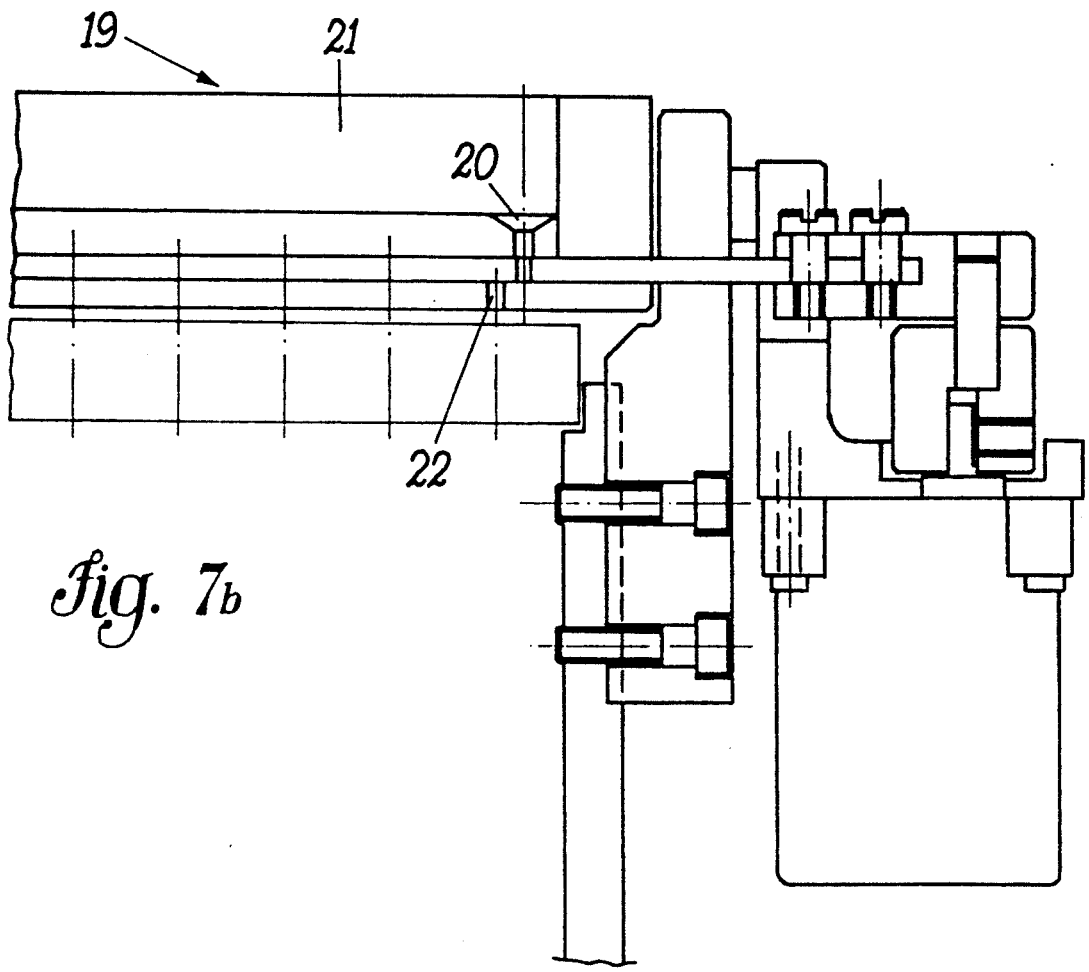
Figure 8B:
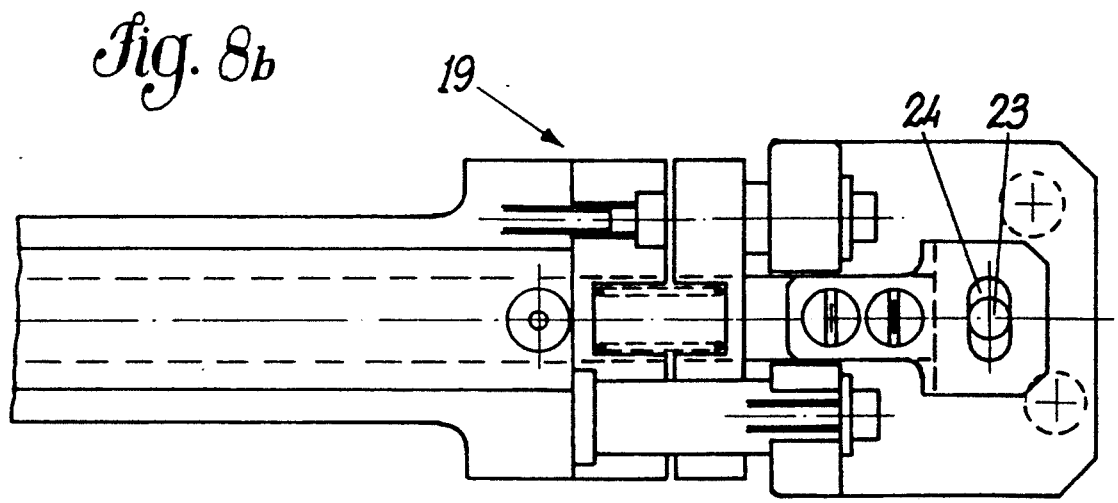

FIGS. 1-3 show the unit of the sucking-dispensing needle 1 that moves on the guide 2 by means of the wheel 3 and of the motor 4.

The needle 1 can move so as to reach the point corresponding to one of the twelve wells of the carrier member 5, the washing station 6 of the sample-bearing test-tube set 7 which are arranged concentrically on the plate 8, and the dilution test-tube set 9a which are arranged concentrically to the set of test-tubes 7 on said plate 8.

The analyzer according to the present invention provides a conveyor unit 9 that carries the carrier member 5, in such a position where it is possible to feed them from the needle 1.

Each of the carrier members 5 are provided with twelve wells 10 for each one of the analyses that are to be performed on the patient's blood.

Figure 4:
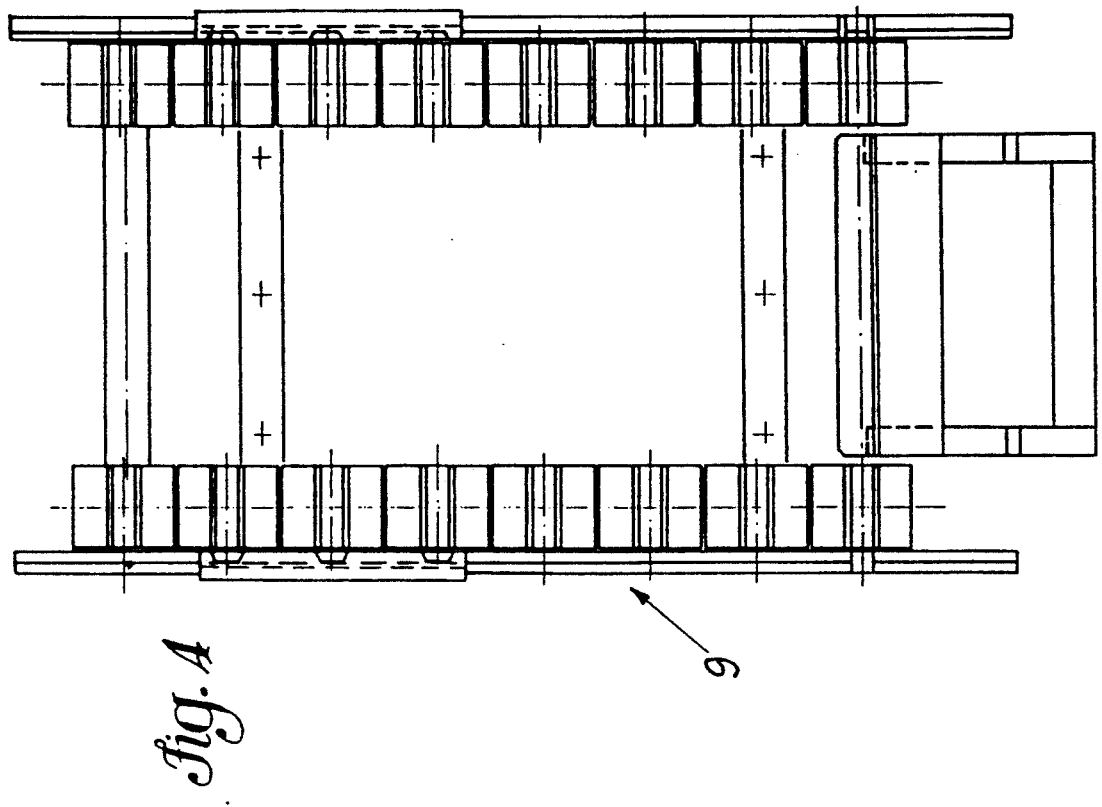
FIG. 4 is a plan view of the conveyor unit of the carrier members according to the invention.

The conveyor unit 9 (FIGS. 4-6) is provided with a pair of wheels 11 that rotate about the axes 12, on which the shaped members 14 are driven by means of the belt 13. Each one of the shaped members 14 has a cavity 15 into which a carrier member 5 is introduced, said carrier member being taken according to pre-established times to the point corresponding to the dispensing zone.

The carrier members 5 are fed practically continuously onto the shaped members 14 by means of three vertical feeders 16 arranged between two plates 17.

Obviously, a motor 18 is provided for causing the unit 9 to rotate and to go forward.

During the forward motion of the members 5 along the conveyor unit 9, two small balls are fed into each one of the wells 10 of said carrier members 5 by means of the gravity feeder 19 (FIGS. 7a, 7b and 8a, 8b).

The feeder 19 is provided with twelve wells 20 in which small metallic balls are arranged, the wells being provided on a longitudinal member 21. The member 21 runs so as to bring the lower outlet of the wells 20 in correspondence to the opening 22 through which the small balls drop into the wells 10 of said carrier members 5.

The feeder 19, while oscillating about the pivot 23 through the groove 24, keeps the balls continuously in motion so that an optimal feeding of said small balls is ensured.

Figure 9:
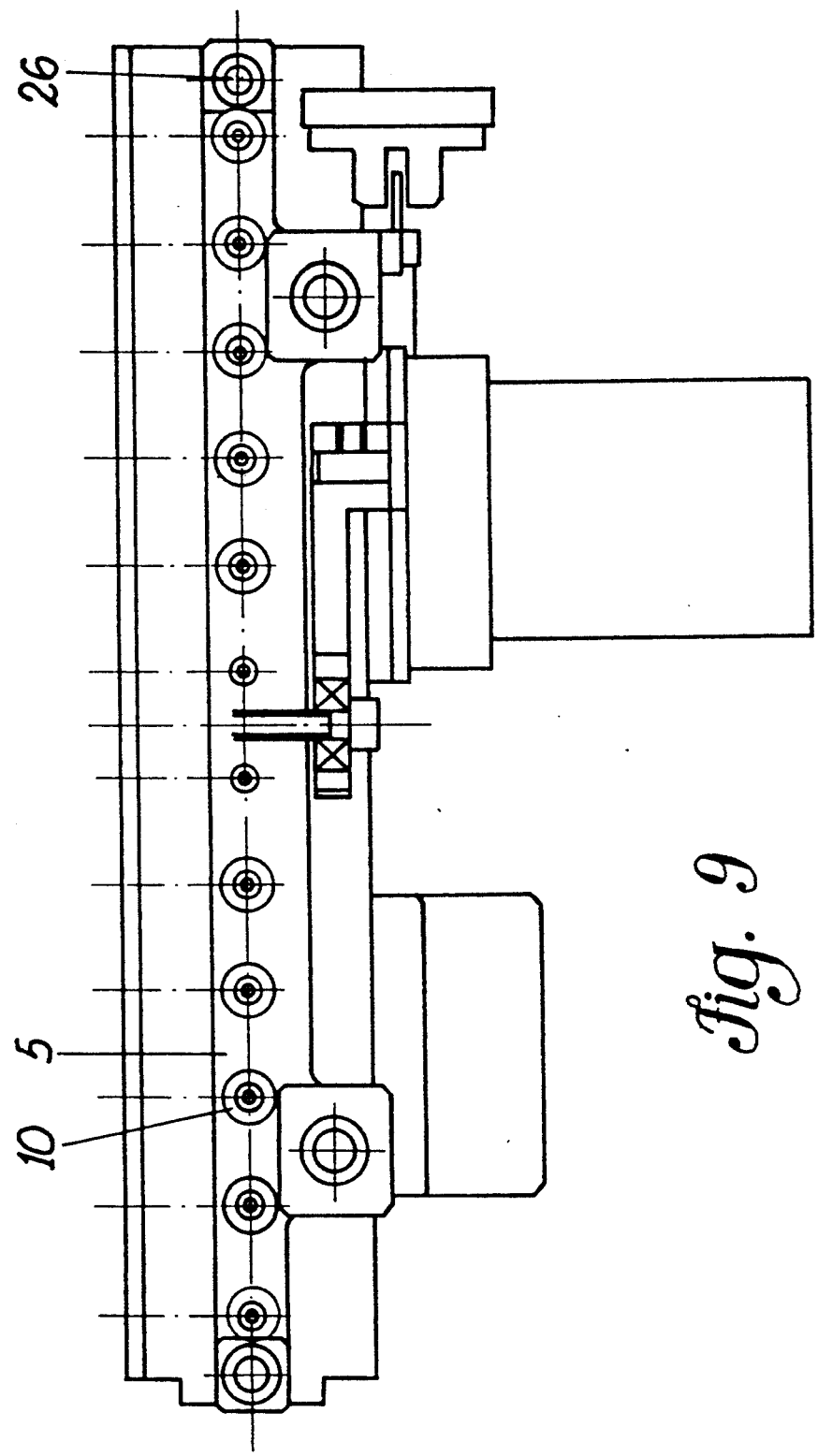
FIG. 9 is a top view of the reading unit of the analyzer according to the present invention.
Figure 10:
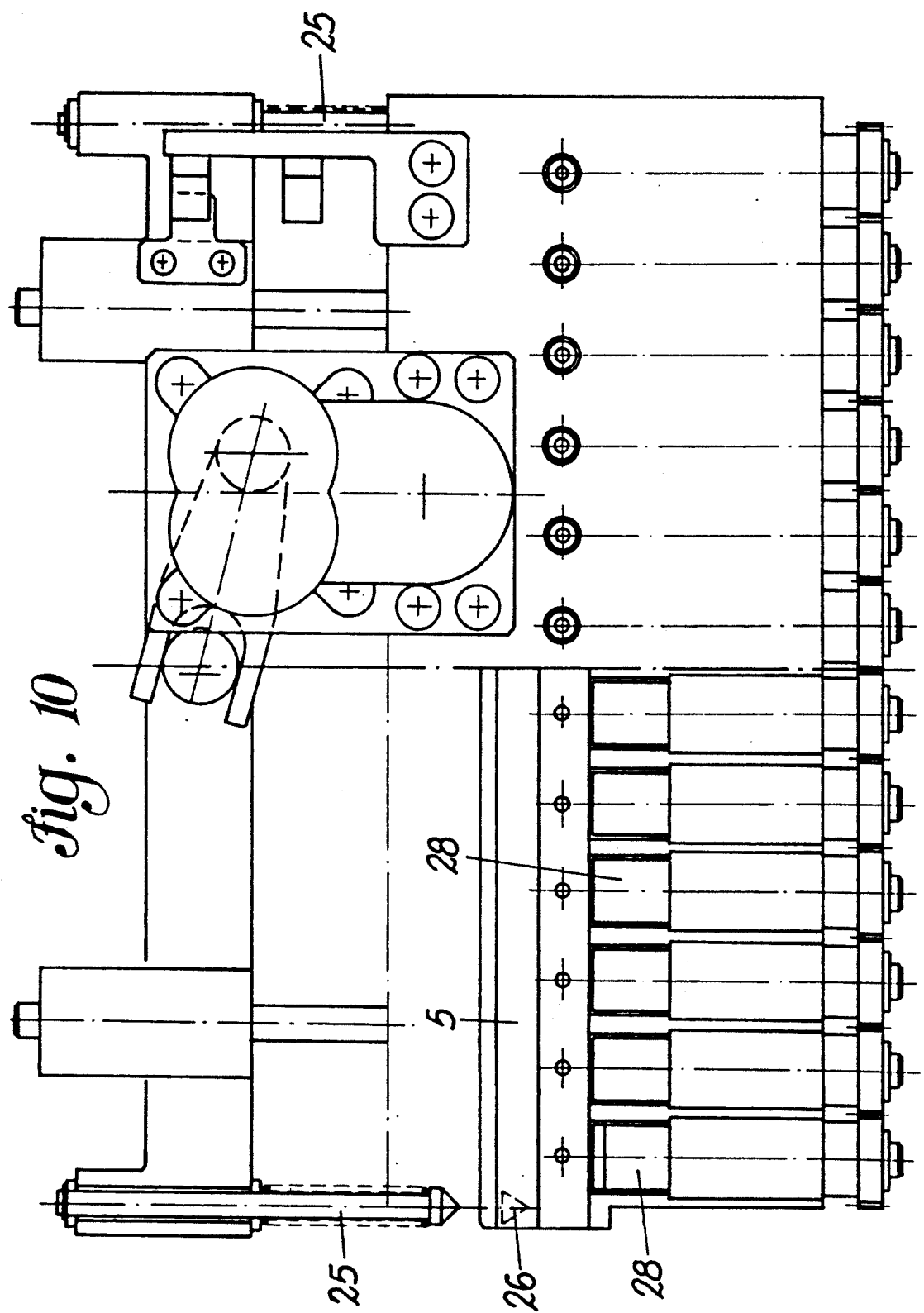
FIG. 10 is a front view of the reading unit of FIG. 9.
Figure 11:
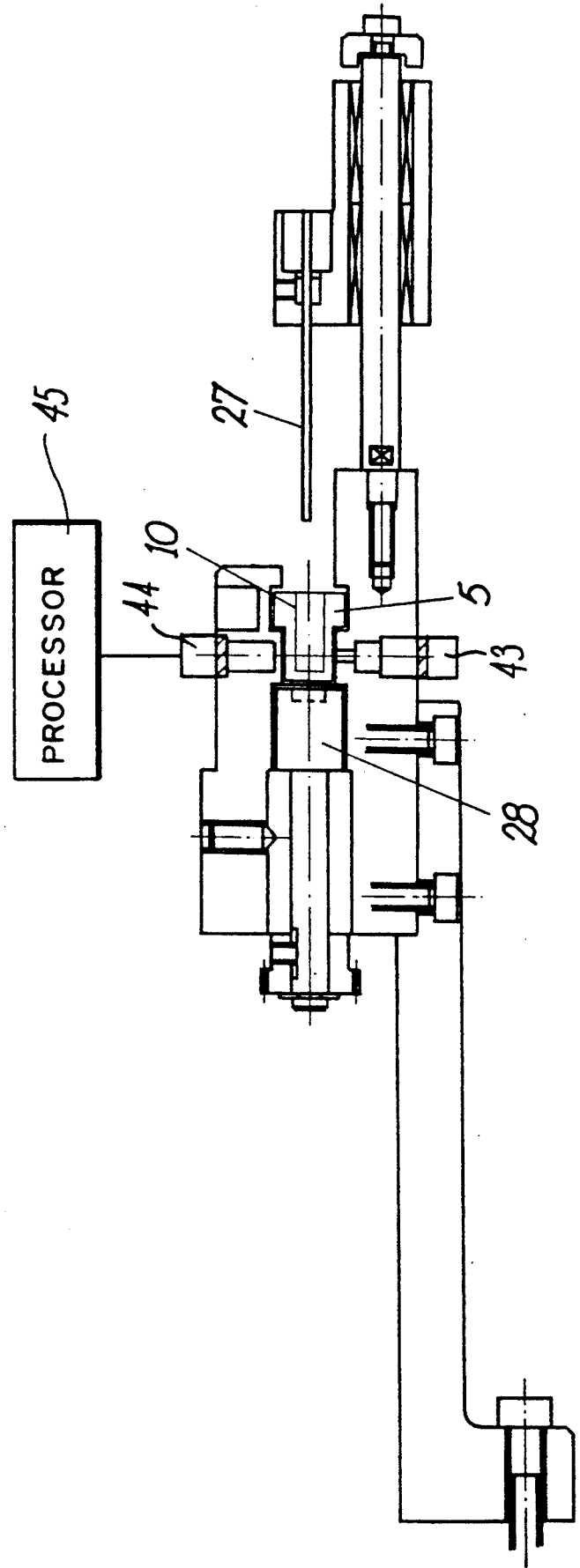
FIG. 11 is a side view of the reading unit of FIG. 9.
Figure 12:
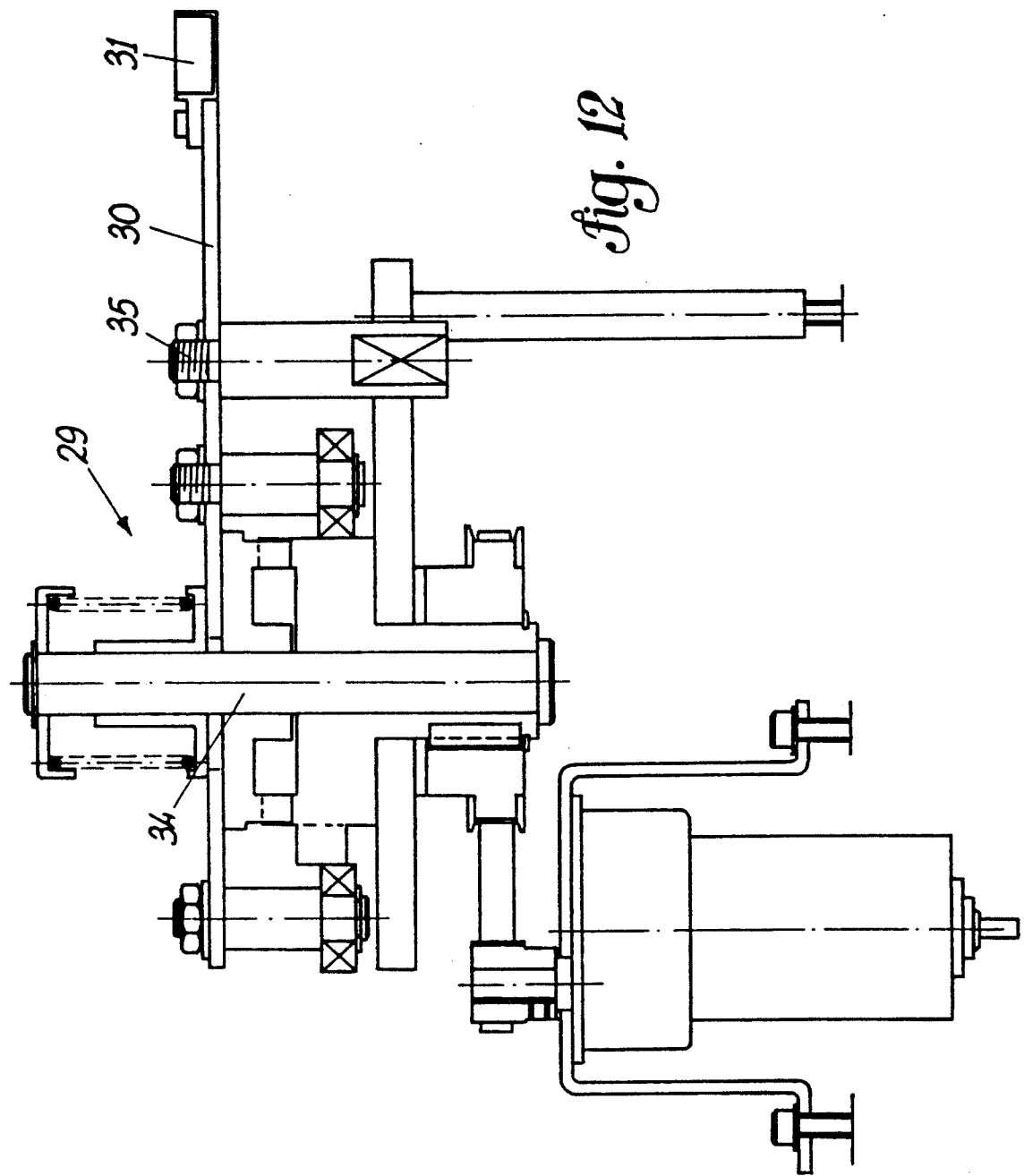
FIG. 12 is a front view of the humidifier unit for wetting the metering needles of antisera.
Figure 13:
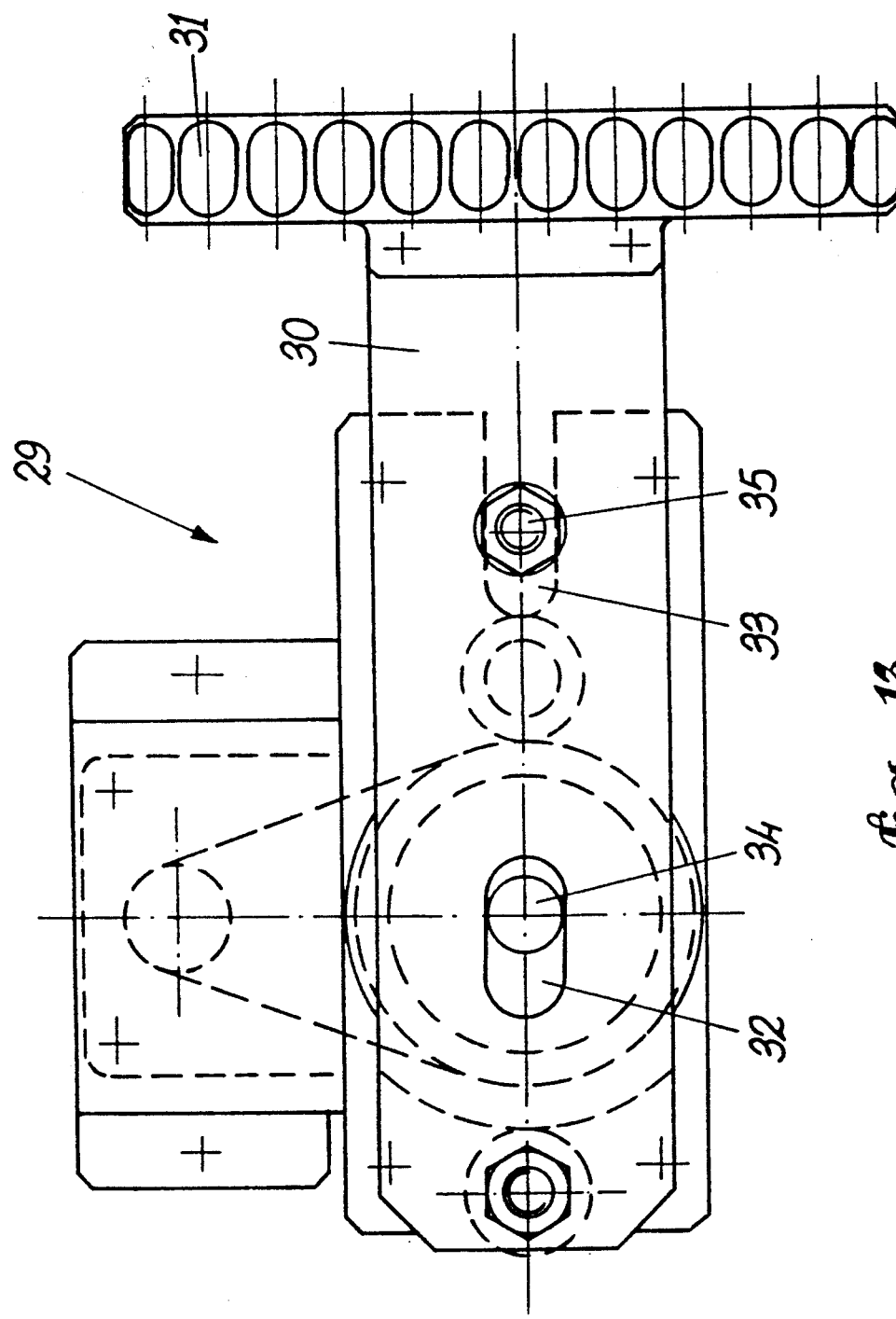
FIG. 13 is a top view of the unit of FIG. 12.
Figure 14:
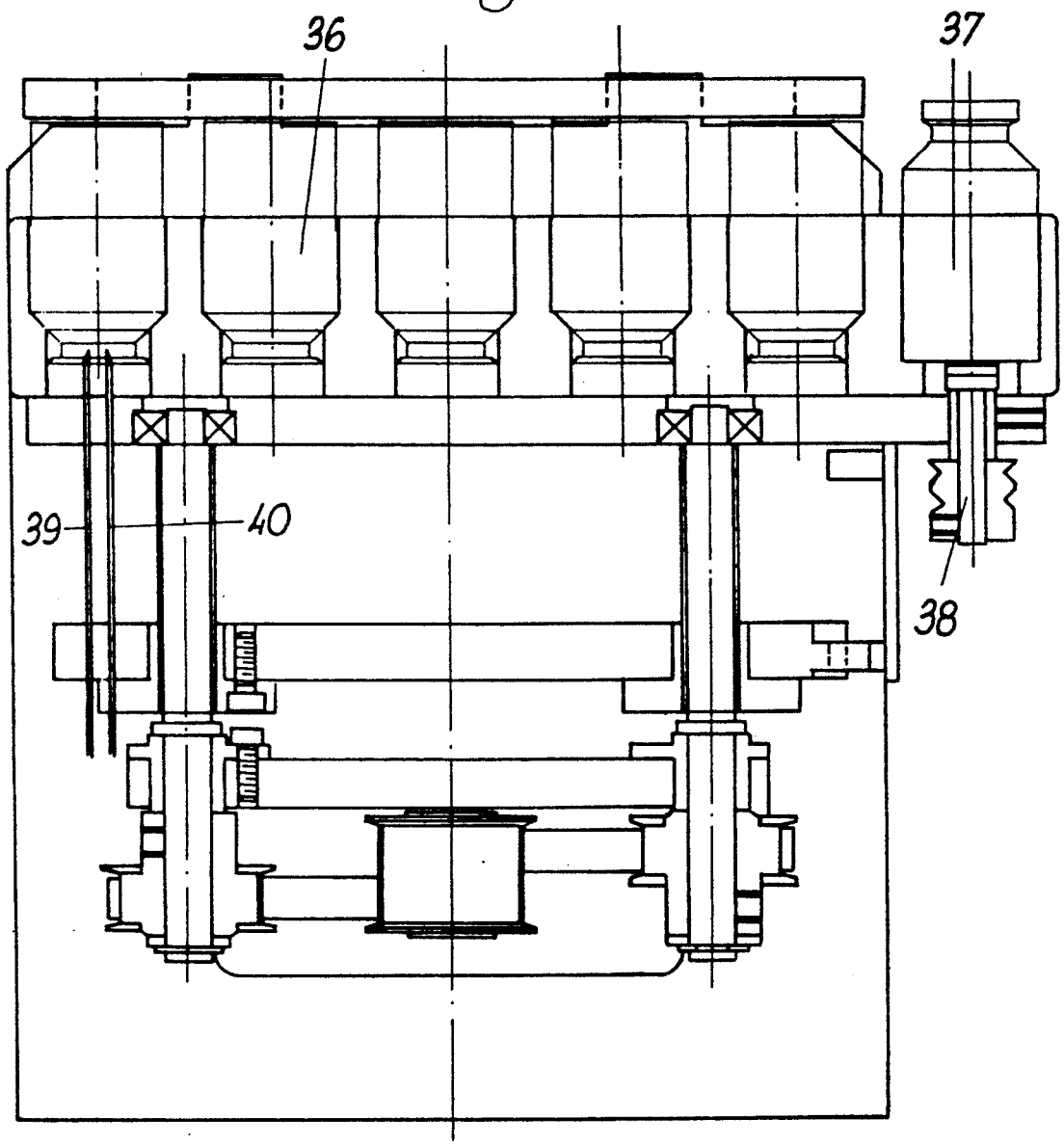
FIG. 14 is a front view of the antisera metering unit of the analyzer according to the present invention.
Figure 15:
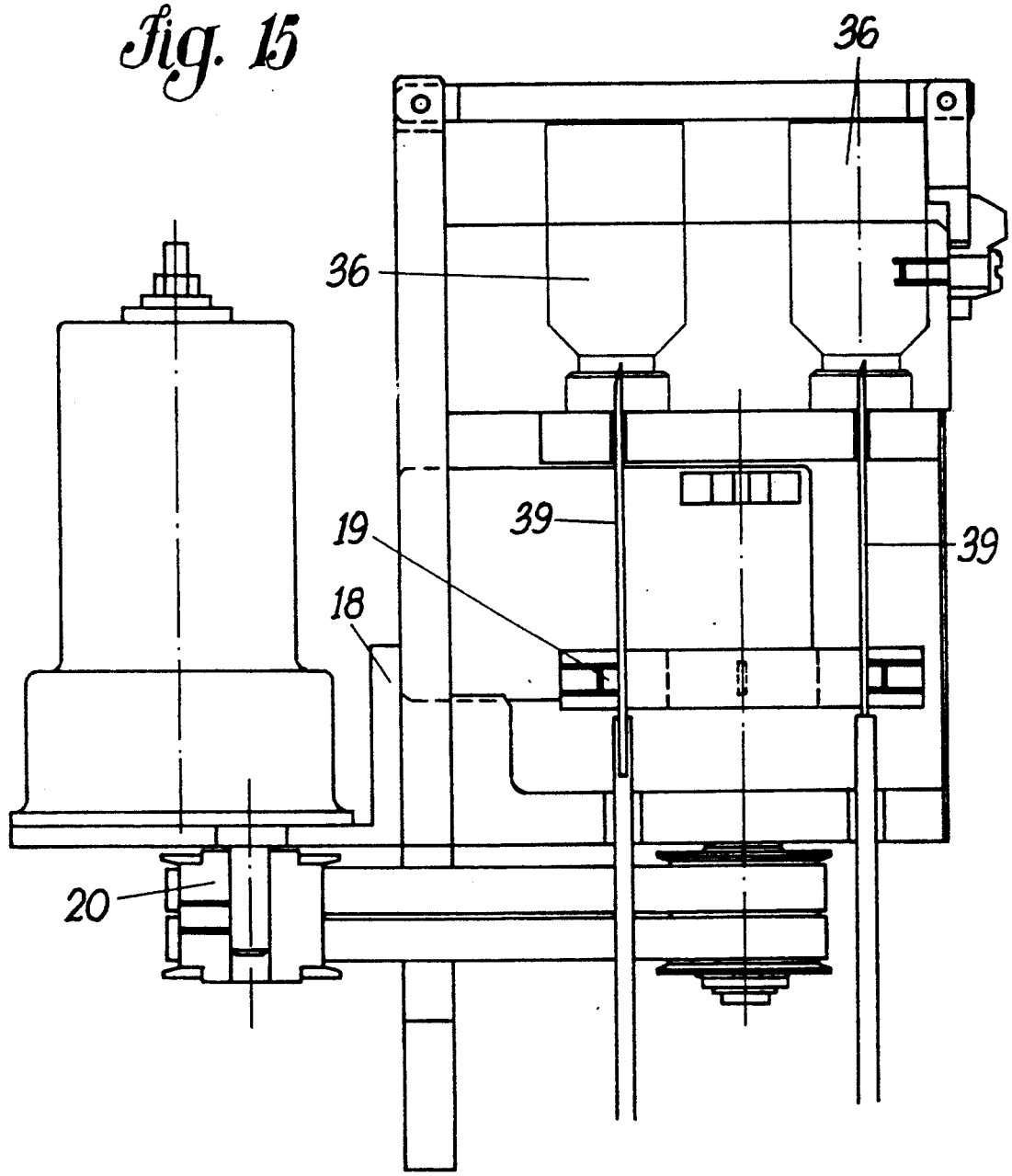
FIG. 15 is a side view of the metering unit of FIG. 14.
Figure 16:
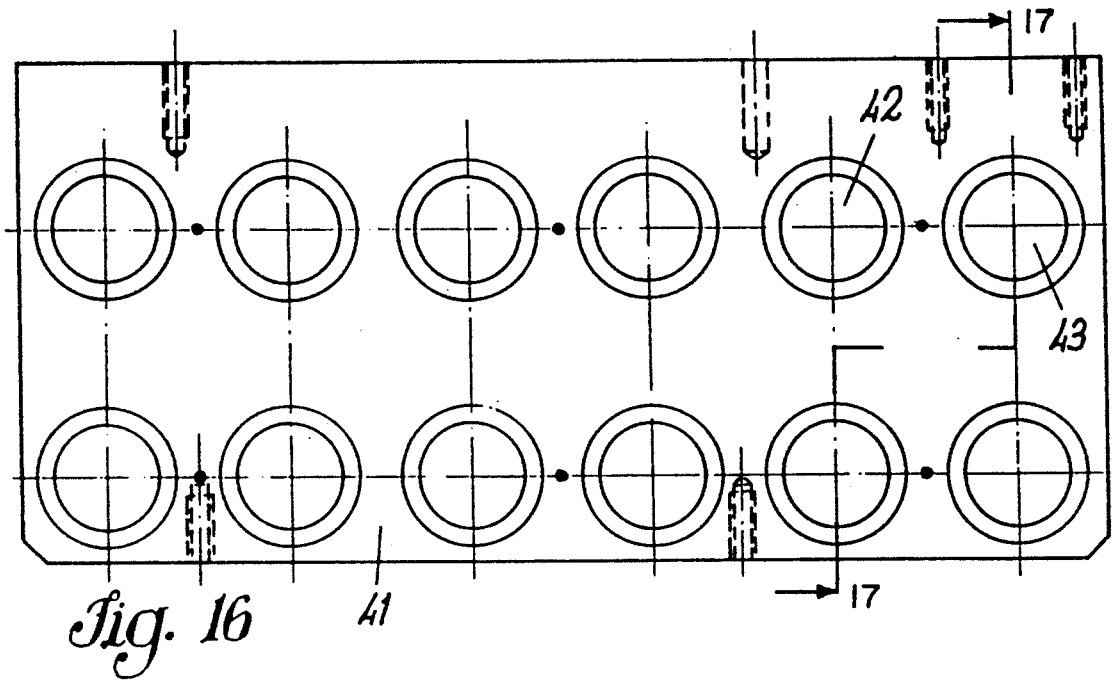
FIG. 16 is a plan view of the bottle support of the metering unit of FIG. 14.
Figure 17:
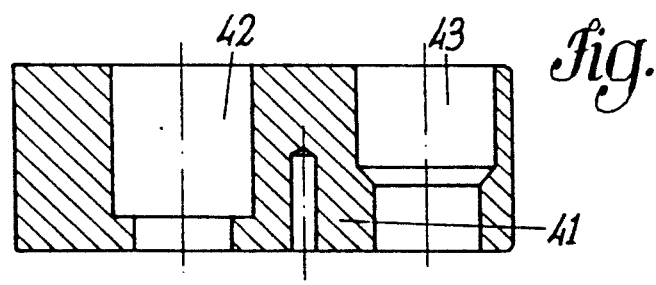
FIG. 17 is a cross-sectional view taken along the line A—A of FIG. 16.
Figure 18:
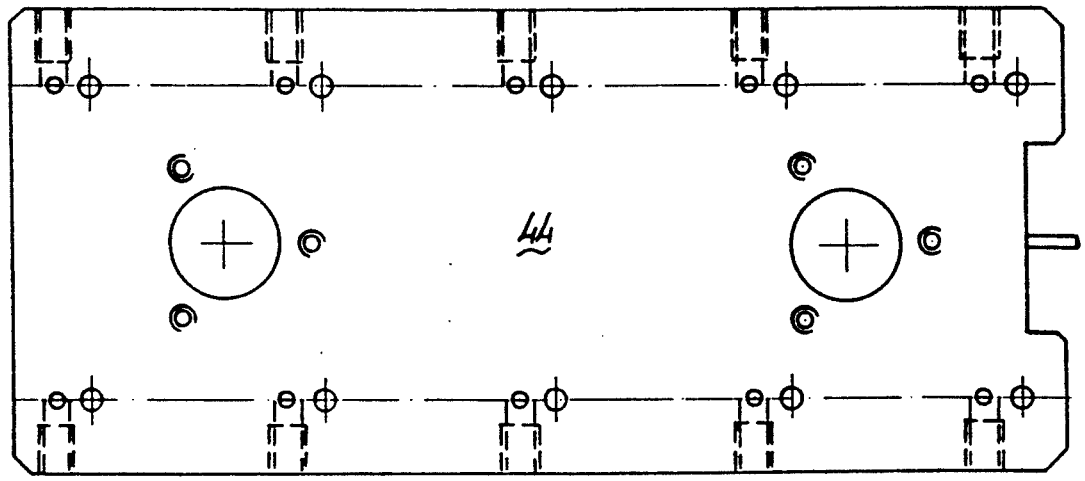
FIG. 18 is a plan view of the needle-bearing plate of the metering unit of FIG. 16.

FIGS. 9-11 show the reading unit of the analyzer according to the present invention.

The reading unit provides a kind of "gangway" for insertion of the carrier members 5 inserts, the samples to be analyzed being put in the wells on such carrier members. The position of the carrier member 5 is mechanically centered by means of the two movable pivots 25 that couple with suitable seats 26 provided at the ends of the carrier member 5 itself.

Before starting the reading step, the specific antiserum for each one of the twelve analyses to be performed is inserted into each well 10 through the needles 27, the feeding of such needles being described below.

During the reading step, the twelve magnets 28 arranged below each well 10 keep said small metallic balls in agitation.

The proper reading is obtained by reading the transmittance of the mixture in each of the twelve wells 10 by means of the twelve corresponding light sources 43 and twelve corresponding reading devices 44 which transmit the data to the processor 45.

A humidifying device 29, which keeps the antisera dispensing needles 27 wet, is provided at the point corresponding to the reading unit.

The device 29 is provided with a slidable plate 30 which has a lifting motion. Twelve cuvettes 31 are provided at the end of said plate 30 corresponding to the reading zone. When the step of using the needles 27 to dispense antisera into the wells 10 has been completed, the plate 30 goes on until the cuvettes 31 reach the carrier member. Then it is lifted until the needles 27 are introduced into the cuvettes 31 themselves.

The plate 30 runs forward because of the grooves 32 and 33 provided on the pivots 34 and 35, while said plate is lifted on the axis 34.

The metering unit, shown in FIGS. 14-18, is provided with ten small bottles 36 containing the antisera and with two small bottles 37 containing the red cells.

Each one of said small bottles 36 and 37 is tightly closed. The small bottles 36 are arranged upside down, and they have a pierceable surface in their lower wall, while the small bottles 37 are kept in the upright position and are stirred continuously by means of the mechanical device 38.

The red cells are sucked out of the small bottles 37, while the antisera are drawn from the small bottles 36 through a drawing system consisting of two needles 39 and 40, one of which is inserted into the small bottle 36 up to a level higher than the level of the antiserum, thus introducing air for allowing the aspiration to be carried out. This system prevents the antisera from being contaminated.

The aspiration is realized through a twelve-channel peristaltic pump and with three motors. If desired, four channels are allowed to operate each time.

The small bottles 36 and 37 are housed on ten housings 42 and two housings 43 of the support 41.

The metering unit also comprises (FIG. 18) a needle-bearing plate 44.

An operative cycle of the analyzer according to the present invention will be described below.

An analyzer according to the present invention is capable of giving 80 complete profiles per hour. The plate 8 carriers 50 sample-bearing test-tube 7 and 50 dilution test-tubes 9.

After activating the computer and setting all analytical parameters in question, the operations are started.

At the test tube feeding unit, a bar code reading device (9b in FIG. 3) is provided to read codes on the sample-bearing test tubes 7. The needle 1 draws the plasma out of the test-tube 7 containing the sample to be analyzed. Then the needle is washed externally at the washing station 6 and it deposits the plasma itself into the first well 10 of the carrier member 5 which is taken to the correct position by the conveyor unit 9.

Then the needle 1 draws the red cells out of the same test-tube 7. The needle is washed externally at the station 6, and it deposits the red cells into one of the dilution test-tubes 9a.

The needle 1 introduces the diluting solution into the same test-tube 9. Then it sucks the mixture of the diluting solution and red cells and deposits the same into the other 10 wells on the carrier member 5.

The needle 1 is then washed internally and externally so it is ready for the next analysis.

The dispensing needle 1 is provided with a sensor (1a in FIG. 3) that allows, when aspirating the plasma out of the test-tube 7, the determination of the moment when it dips into the same. This allows this step to be carried out in a way functionally independent of the height of the sample level in the test-tubes, as a minimum level is sufficient.

For sucking the red cells out, these problems do not arise because the aspiration occurs at the bottom of the test-tubes 7.

The wells in the carrier member 5 into which the needle 1 introduces plasma and the dilution solution and red cells have already been fed with small balls through the feeder 19.

When the step of filling the wells 10 has been completed, the carrier member 5 is transferred to a point corresponding to the position of the reading unit where it is centered by the two movable pivots 25.

Red cells are introduced into the wells 10 containing the plasma and antiserum is introduced by needles 27 into the wells 10 containing the diluting solution and red cells. During this step, the small balls are kept in motion by the magnets 28.

Then the reading of the transmittance of each well 10 is carried out in a horizontal direction by the optical system including a light source S and a light sensor L. The result is transferred to the processor which generated the data through suitable software.

As is well known, antiserum and red cells belonging to the same unit have a tendency to become agglutinated, so that the solution within the well 10 has a tendency to become clear, and the reading device, on comparing the transmittance from the mixing time on, allows the obtainment of a true reading of the result.

Software has been designed for controlling the analyzer, said software being capable of optimally controlling the operation of the apparatus and the issuing of the results, signalling any kind of error, and inviting the operator to repeat the determination in case of doubt.

The software controls the analytical part and the operation of motors and of stop photocells. It also controls the brightness of the optical beam and receives the reading data.

A series of control operations is provided in order to avoid the possibility of occurrence of errors under operative conditions during in the operation of the machine. Safety standards (CEI-IEC 62 D-WG5) have been particularly taken into consideration in order to avoid damages to operators due to the numerous members in motion.

The closure of all doors and movable parts that are to be opened to allow the introduction of samples and reagents and the maintenance of the analyzer is also controlled.

If even one only door is shown to be open, the machine cannot start operating and it asks the operator to check the closure of the movable parts mentioned above.

The control software also checks the emergency buttons present, blocking instantaneously all movements in case they are pushed.

The data processing software processes the input data and the graphic data of each channel. It compiles the final report, checking the various possible and negative conclusions over the twelve channels.

It is possible to modify this part of the software so that the curve of the graphic data is the best fit for the specific requirements.

Particular care has been given to the processing of data to avoid the possibility of even a partially erroneous result. If just a single reaction among the twelve reactions is in doubt, the software does not give any result, thus putting the operator on guard as regards the particular occurrence.

The operator can decide on the basis of the graphic data whether to accept the result or to repeat the analysis.

The data are then stored and can be employed on-line for any possible statistical or research applications.

The present invention has been disclosed according to some preferred embodiments of the same, but it is to be understood that modifications and/or changes can be introduced in the same by those who are skilled in the art without departing from the spirit and scope of the invention for which a priority right is claimed.

We claim:

1. Apparatus for analyzing blood samples to determine the ABO group and the phenotype of blood by introducing an agglutinizing solution into samples taken from blood, comprising, a plurality of carriers each provided with at least four reaction and reading wells;

a tube-holding unit for holding a first group of test tubes which contain blood and a second group of test tubes which are used for diluting samples which contain constituents of the blood;

a carrier-loading station provided with a dispensing needle, means for moving the dispensing needle to positions which include (i) a washing station where the needle is washed, (ii) a sample-drawing position where the needle is positioned to draw a sample from a test tube in the first group, (iii) a sample-diluting position where the needle is positioned to introduce a dilution solution into a test tube in the second group, (iv) a position where the needle is positioned to introduce fluid drawn from one of said test tubes into the reaction and reading well;

a reading unit provided with optical means for reading the optical transmittance in each of said reaction and reading wells in a carrier, commencing when the agglutinizing solutions are introduced into the reaction and reading wells;

a conveyor unit for moving said carriers from a first position where their respective reaction and reading wells receive fluid from the dispensing needle to a second position at the reading unit;

ball feeding means for feeding small balls into said reaction and reading wells of carriers on said conveyor unit;

a metering unit for feeding, into said reaction and reading wells, agglutinizing solutions which are capable of producing an agglutinizing reaction with contents in some reaction and reading wells as a function of blood type; and, a processor for providing data which is a function of the optical transmittance in said reaction and reading wells as sensed by the reading unit during the agglutinizing reaction.

2. Apparatus according to claim 1 wherein each carrier includes twelve reaction and reading wells.

3. Apparatus according to claim 1 wherein said carriers are elongated and the reaction and reading wells are arranged side-by-side along the lengths of such carriers.

4. Apparatus according to claim 1 wherein the conveyor unit includes an endless drive member provided with seats for receiving said carriers.

5. Apparatus according to claim 4 wherein the carriers are provided with vertical projections, and the conveyor unit has seats for receiving said projections.

6. Apparatus according to claim 1 wherein the ball feeding means is mechanically oscillated and is operable to deposit said balls, by gravity, into said reaction and reading wells before the respective carriers arrive at said dispensing needle.

7. Apparatus according to claim 6 wherein the ball feeding means is operable to feed two balls into each of said reaction and reading wells.

8. Apparatus according to claim 1 wherein the metering unit includes a bottle-carrying plate provided with means for holding ten antisera bottles and two red cell bottles, means for sucking antisera and red cells from the bottles, said apparatus having one needle for sucking antiserum from a bottle and another needle for introducing air into the bottle above the antisera, and means for agitating the red cell bottles.

9. Apparatus according to claim 1 wherein the metering unit includes a bottle-carrying plate provided with means for holding ten antisera bottles and two red cell bottles, means for sucking antisera and red cells from the bottles, said apparatus having one needle for sucking antiserum from a bottle and another needle for introducing air into the bottle above the antisera, and means for agitating the red cell bottles, said carrier having twelve reaction and reading wells, and said metering unit having twelve needles for feeding agglutinizing solutions into said reaction and reading wells.

10. Apparatus according to claim 9 wherein the metering means includes a peristaltic pump having twelve channels for sucking antisera and red cells from the bottles.

11. Apparatus according to claim 9 including a humidifying device for wetting the needles in an area where the needles feed the agglutinizing solution into said reaction and reading wells, said humidifying device including humidifying cuvettes which are mechanically moved horizontally and vertically.

12. Apparatus according to claim 1 including means for centering the carriers at the reading unit.

13. Apparatus according to claim 12 wherein the centering means includes two movable pistons which engage said carriers.

14. Apparatus according to claim 1 including magnets which are moved below the reaction and reading wells at the reading unit to keep said balls in motion in the reading zone.

15. Apparatus according to claim 1 wherein the tube-holding unit includes a rotatable plate with two concentric arrays of test tubes.

16. Apparatus according to claim 1 including a code reading means for reading data on test tubes in said tube-holding unit.

17. Apparatus according to claim 16 wherein the code reading means is a bar code reader.

18. Apparatus according to claim 1 including means on the dispensing needle for detecting the dipping of the needle into a sample.

19. Apparatus according to claim 1 including means for imparting motion to said balls when they are in their respective reaction and reading wells.

20. Apparatus according to claim 19 wherein the means for imparting motion to said balls includes magnets.

21. Apparatus for analyzing blood samples to determine the ABO group and the phenotype of blood by introducing an agglutinizing solution into samples taken from blood, comprising, means for holding test tubes which contain blood samples;

a carrier having wells in which agglutination reactions are performed;

means for transferring blood constituents from said test tubes to said wells, means for introducing a reaction solution into said wells to produce agglutination reactions with blood constituents in at least some of said wells;

optical means for sensing the optical transmittance of contents of said wells simultaneously with the occurrence of agglutination reactions in said wells, said optical means having an optical axis with a horizontal component through a said well to sense optical transmissivity indicative of an agglutination reaction.

* * * * *